US010206725B2

(12) United States Patent
Vasta et al.

(10) Patent No.: US 10,206,725 B2
(45) Date of Patent: Feb. 19, 2019

(54) ORTHOPEDIC VARIABLE SCREW FIXATION MECHANISM

(71) Applicant: Gramercy Extremity Orthopedics, LLC, Richardson, TX (US)

(72) Inventors: Paul J. Vasta, Richardson, TX (US); Michael G. Thomas, Richardson, TX (US)

(73) Assignee: Gramercy Extremity Orthopedics LLC, Richardson, TX (US)

( * ) Notice: Subject to any disclaimer, the term of this patent is extended or adjusted under 35 U.S.C. 154(b) by 0 days.

(21) Appl. No.: 15/742,386

(22) PCT Filed: Dec. 6, 2016

(86) PCT No.: PCT/US2016/065171
§ 371 (c)(1),
(2) Date: Jan. 5, 2018

(87) PCT Pub. No.: WO2017/100196
PCT Pub. Date: Jun. 15, 2017

(65) Prior Publication Data
US 2018/0263671 A1   Sep. 20, 2018

Related U.S. Application Data

(60) Provisional application No. 62/263,729, filed on Dec. 6, 2015.

(51) Int. Cl.
*A61B 17/80* (2006.01)
*A61B 17/86* (2006.01)
*A61B 90/00* (2016.01)

(52) U.S. Cl.
CPC ........ *A61B 17/8047* (2013.01); *A61B 17/808* (2013.01); *A61B 17/8057* (2013.01); *A61B 17/863* (2013.01); *A61B 2090/0811* (2016.02)

(58) Field of Classification Search
CPC .................................................. A61B 17/8047
See application file for complete search history.

(56) References Cited

U.S. PATENT DOCUMENTS 6,206,881 B1 *   3/2001   Frigg ................. A61B 17/8052
                                                             606/291
6,663,632 B1 *  12/2003   Frigg ..................... A61B 17/80
                                                             606/246

(Continued)

FOREIGN PATENT DOCUMENTS

EP            1768584 B1     10/2011

*Primary Examiner* — Zade Coley
(74) *Attorney, Agent, or Firm* — Panitch Schwarze Belisario & Nadel LLP

(57) ABSTRACT

A sliding plate variable angle locking mechanism includes a bone plate, a first sliding plate, a locking ring and a bone screw. The bone plate includes a plate cavity, a bone plate surface and a shelf. The plate hole defines a plate hole diameter. The first sliding plate a central hole that defines a sliding plate hole diameter. The sliding plate hole diameter is smaller than the plate hole diameter. The first sliding plate is positioned in the plate cavity in an assembled configuration. The locking ring is movably mountable to the bone plate. The locking ring hole diameter is greater than the sliding plate hole diameter. The bone screw head diameter is greater than the sliding plate hole diameter. The head threads are configured to form internal threads in the central hole of the first sliding plate when the bone screw is driven into the first sliding plate.

20 Claims, 9 Drawing Sheets

(56) References Cited

U.S. PATENT DOCUMENTS

| | | | |
|---|---|---|---|
| 7,686,837 B2 * | 3/2010 | Gasser | A61B 17/8047 606/287 |
| 2004/0073218 A1 * | 4/2004 | Dahners | A61B 17/8057 606/287 |
| 2006/0241618 A1 * | 10/2006 | Gasser | A61B 17/8047 606/287 |
| 2007/0083203 A1 | 4/2007 | Ribeiro | |
| 2009/0182383 A1 * | 7/2009 | Prybyla | A61B 17/8047 606/280 |
| 2011/0015682 A1 | 1/2011 | Lewis et al. | |
| 2013/0184765 A1 * | 7/2013 | Beyar | A61B 17/8052 606/281 |

\* cited by examiner

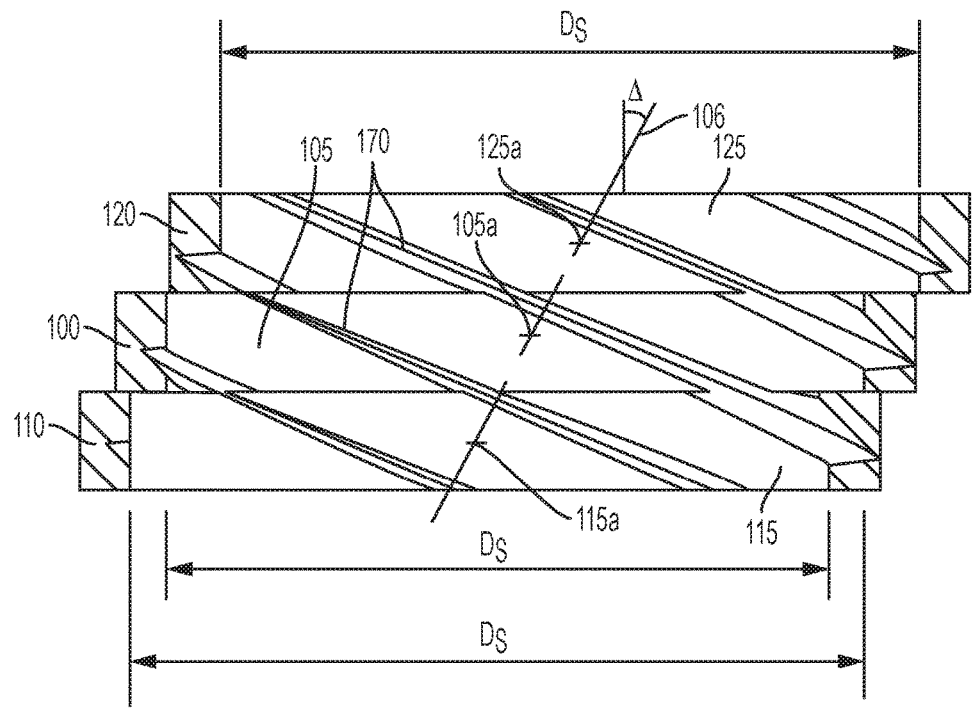
FIG. 3c
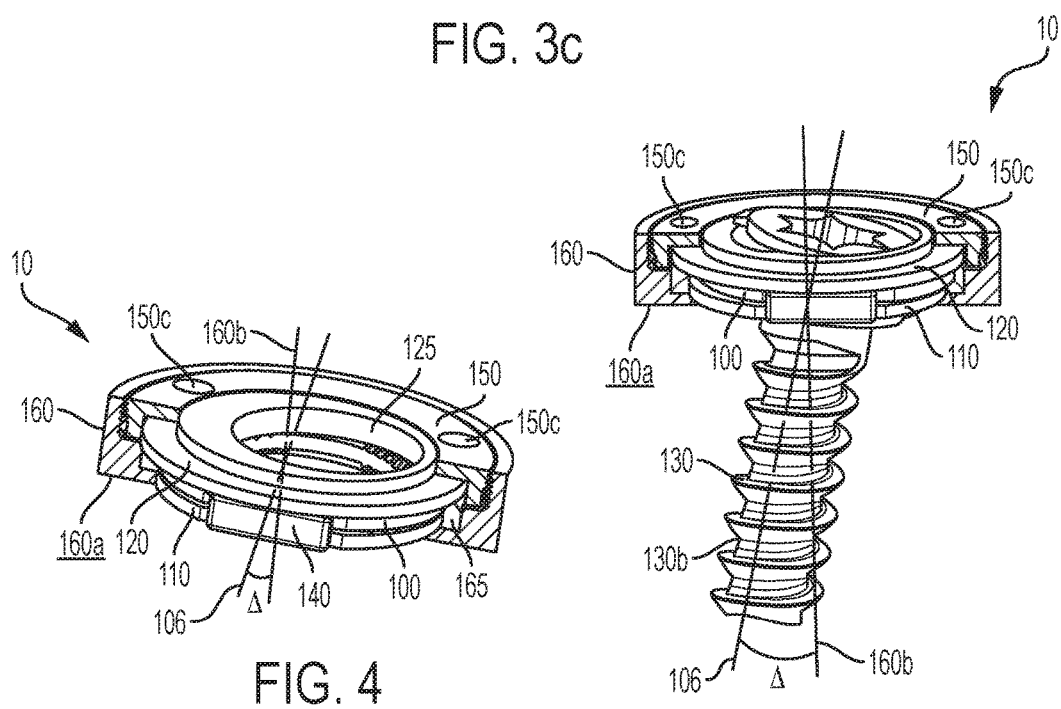
FIG. 4
FIG. 5

ORTHOPEDIC VARIABLE SCREW FIXATION MECHANISM

CROSS REFERENCE TO RELATED APPLICATIONS

This application claims priority to U.S. Provisional Patent Application No. 62/263,729, filed on Dec. 6, 2015, entitled "Orthopedic Variable Screw Fixation Mechanism," the entire contents of which are incorporated herein by reference in its entirety.

BACKGROUND OF THE INVENTION

In situations where bone fixation occurs near a joint and the surgeon desires to angle the screw to avoid encroachment into the joint, where the surgeon wishes to intentionally angle a screw to cross a fracture gap or joint in order to achieve fusion, or other surgical applications where intentional screw angulation is useful, it is desirable to insert the fixation screw at an angle offset from the central axis of the screw hole in the bone plate and an orientation directed radially about the circumference of the hole. In addition, there are clinical circumstances in which rigidity of fixation is desired, specifically between the screw and the plate, where it is desirable for forces acting on the bone to be counteracted in part or in whole by the screw-plate construct. In these situations, it is desirable to provide a system or mechanism for rigidly locking the screw to the plate where the shaft of the screw can be fixed at various angles to the central axis of the counterpart hole in the plate and at various orientations about the circumference of the screw hole. This type of plate/screw construct is known in orthopedics as a variable-angle locking screw or plate.

Variable angle locking in orthopedic applications is known and utilizes various mechanical designs to secure the head of the bone screw to the plate hole and arranging the shaft and head of the bone screw at variable angles relative to the plate. These designs include plate holes with tapped tabs that cross-thread, self-tapping plate/screw constructs, and frictional "crush-lock" features that provide a degree of rigidity between the plate and screw. However, each of these designs is limited in the strength of the interface between the screw head and the plate due to the reduced surface contact area, and/or reduced mechanical advantage, specific to these features. The tabbed cross-threading and self-tapping designs, for example, include locking features that are a machined as part the plate and thus fixed in position and orientation. To provide a rigid support for a locking screw, the design of the locking mechanism must be optimized for a single screw angle, usually orthogonal to the plate. Deviation from this angle will reduce the surface contact area between the plate and screw therefore reducing the resulting rigidity of the inter-connection. Additionally, placing a screw at the angular limit of the locking mechanism can increase the difficulty of inserting and locking the screw to the plate, further reducing the clinical comfort and confidence of use.

It would be desirable to design, develop and implement a variable angle locking design that enables an orthopedic bone fixation plate to allow a screw to be placed into the bone at various angles, both offset to the plate hole central axis and at radial orientations about the hole circumference, with the same mechanical interface and, therefore, strength, at all angles of screw fixation. This is somewhat achieved with the crush-lock mechanisms found primarily in pedicle screw fixation for spinal applications, however these designs are substantially weaker than the tabbed cross-thread or self-tapping designs when used in plates that are dimensioned for long or small bones (i.e., lacking sufficient depth), if not entirely impractical altogether in that application. The preferred invention disclosed herein improves the strength and rigidity of known variable angle locking plate mechanisms by providing an increased contact area between the screw head threads and the plate regardless of the angle of offset.

BRIEF SUMMARY OF THE INVENTION

The preferred present invention relates to an orthopedic implant for use in repairing fractured bone and/or bone that has undergone a surgical procedure for therapeutic purposes, e.g., deformity correction, reconstruction, arthrodesis, etc. The preferred implant described herein refers more specifically to an orthopedic bone fixation plate and screw construct having variable angle and locking capabilities with a locking strength between the screw and plate that is superior to prior art variable angle locking systems. The preferred invention described herein provides a novel means for accommodating variable angle locking of a bone screw to an orthopedic plate.

Briefly stated, the preferred sliding plate variable angle locking mechanism includes a bone plate, a first sliding plate, a locking ring movably mountable to the bone plate and a bone screw having a head with head threads and a shaft. The bone plate includes a plate cavity, a bone plate surface, a plate hole adjacent the bone plate surface and a shelf formed in the plate cavity proximate the plate hole. The plate hole defines a plate hole diameter. The first sliding plate has an upper surface, a lower surface and a central hole. The central hole defines a sliding plate hole diameter. The sliding plate hole diameter is smaller than the plate hole diameter. The lower surface of the first sliding plate is positioned in the plate cavity in an assembled configuration. The first sliding plate is configured for slidable movement within the plate cavity. The locking ring is movably mountable to the bone plate. The locking ring has a locking ring hole. The locking ring hole defines a locking ring hole diameter. The locking ring hole diameter is greater than the sliding plate hole diameter. The head has head threads that define a bone screw head diameter. The bone screw head diameter is greater than the sliding plate hole diameter. The head threads are configured to form internal threads in the central hole of the first sliding plate when the bone screw is driven into the first sliding plate in the plate cavity.

The preferred invention described herein includes one or more sliding plates incorporated into a bone fixation plate hole for the purpose of providing rigid fixation of a bone screw to the plate at various angular orientations relative to the central axis of the plate hole. The sliding plates contain a central opening and are positionable within the bone fixation plate hole such that the center of the opening may align with the axis of the screw shaft in its desired orientation relative to the fixation plate. For example, a screw is positioned at an angle relative to the central axis of the fixation plate hole such that the intersection of the screw axis and the hole axis is located at a midpoint between the top and bottom surface of the fixation plate. If a sliding plate is located above the intersection point, the center of the opening of the sliding plate would be offset from the intersection point along the screw axis in the direction of the screw head. Likewise, if a sliding plate is located below the intersection point, the center of the opening of the sliding plate would be offset from the intersection point along the screw axis in the direction opposite of the screw head. It can be understood, therefore, that given a plurality of sliding plates with one above and the other below the intersection point, the centers of the sliding plate openings would form a line concurrent with the screw axis. Given this configuration, it also can be understood that providing a threaded lock feature interconnecting the sliding plates and the screw head would allow the screw head to be fixed to both of the sliding plates thus providing greater contacting surface area and therefore increased fixation.

To provide the rigidity between the screw and the plate, the sliding plates are preferably, rigidly secured to the screw and the plate in a mounted configuration, as they form the connection that bridges the two. The preferred invention described herein provides a rigid connection between the plate hole and the sliding plates in the mounted configuration, utilizing surface friction applied by various means of force acting on the sliding plates.

In a preferred embodiment, two sliding plates are positioned within a bone fixation plate hole. The bottom of the bone fixation plate hole, continuous with the bone-facing surface of the bone fixation plate, contains a flange with a central hole. A compression means, in one embodiment provided by threading a locking ring onto the upper portion of the bone fixation plate hole thereby compressing the two sliding plates together and against the bone fixation plate hole flange, operates to increase the friction between the sliding plates and the plate hole flange to a level sufficient to provide the necessary fixation rigidity.

In an alternative embodiment, the center of the bone fixation plate hole contains a flange with a central hole. The flange is flat and recessed from both the top and bottom surfaces of the plate by a depth equal to or greater than the thickness of the sliding plates. In an uncompressed state, the friction between the sliding washers and the bone fixation plate hole flange is sufficiently low to allow the sliding plates to be positioned within the hole such that their central holes are aligned with the axis of the screw. A compression mechanism, in one embodiment is provided by the threading of the screw head into the bottom sliding plate hole thereby compressing the two sliding plates together and against the bone fixation plate hole flange, operates to increase the friction between the sliding plates and the plate hole flange to a level sufficient to provide the necessary fixation rigidity.

In a procedure in which such a sliding plate construct is used, the orthopedic bone fixation plate is positioned on a bone at a location conducive to affecting the desired fixation. A drill is used to create a hole in the bone at the desired angle relative to the plate and along a trajectory that approximately intersects the center of the bone fixation plate hole. A screw is inserted into the bone fixation plate hole and is threaded into the bone, guided by the previously drilled hole. The sliding plates align their centers with the screw axis, sliding into position as the screw shaft passes through. The head of the screw then enters the sliding plate and is locked in place by various means of imparting a force onto the sliding plate as described below, thereby rigidly fixing the sliding plate(s) to the bone fixation plate and the sliding plate(s) to the screw. With the screw head fully inserted into the sliding plate(s), the entire construct becomes rigidly locked in place along every degree of freedom.

BRIEF DESCRIPTION OF THE SEVERAL VIEWS OF THE DRAWINGS

The foregoing summary, as well as the following detailed description of preferred embodiments of a sliding plate variable angle locking mechanism and method of the present preferred invention, will be better understood when read in conjunction with the appended drawings. For the purposes of illustrating the sliding plate variable angle locking mechanism, there are shown in the drawings preferred embodiments. It should be understood, however, that the preferred invention is not limited to the precise arrangements and instrumentalities shown. In the drawings:

FIG. 3c is a magnified cross-sectional view of the sliding plates and the rotating plate of FIG. 3b, wherein the bone fixation screw is removed and tapped threads from the bone fixation screw are shown;

FIG. 4 is a partial cross-sectional, top perspective view of the sliding plate variable angle locking mechanism of FIG. 1, showing the sliding plates, an upper rotating plate, and a locking ring in the locked configuration with the bone screw removed for clarity;

FIG. 5 is a partial cross-sectional, top perspective view of the sliding plate variable angle locking mechanism of FIG. 1 that is similar to the view of FIG. 4 and includes the bone screw fixed in the sliding plate variable angle locking mechanism;

FIG. 9a is a top plan view of the sliding plate variable angle locking mechanism of FIG. 8a;

DETAILED DESCRIPTION OF THE INVENTION

Figure 1:
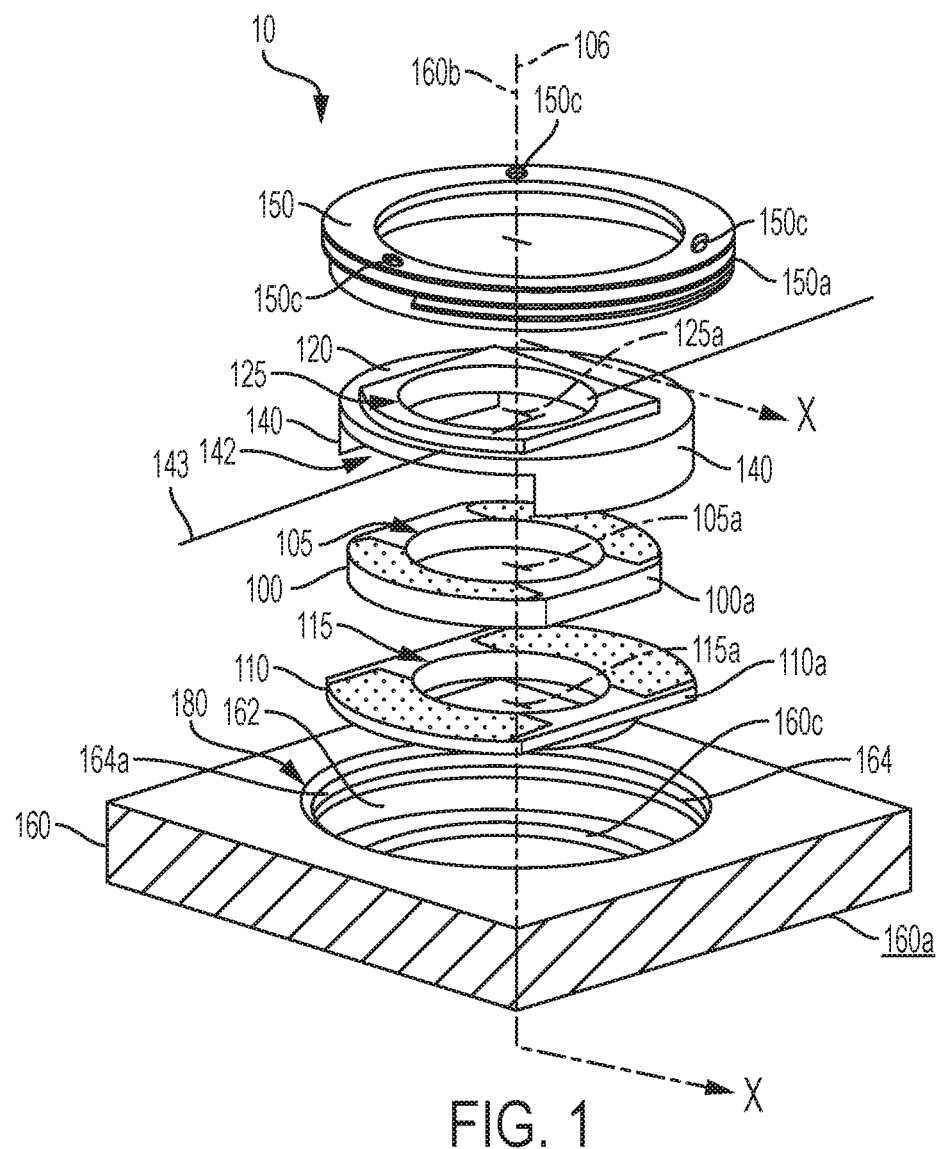
FIG. 1 is an exploded, top perspective view of a first preferred embodiment of the sliding plate variable angle locking mechanism, showing two sliding plates, an upper rotating plate, a locking ring, and a portion of a bone fixation plate.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred embodiments of the sliding plate variable angle locking mechanism and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-13, preferred embodiments of the invention described herein are directed to a sliding plate variable angle locking mechanism, generally designated 10, 20, 30, 40, 50, 60, 70, 80. The preferred embodiments of the sliding plate variable angle locking mechanisms 10, 20, 30, 40, 50, 60, 70, 80 are comprised of a mechanical assembly for locking a bone fixation screw 130 to an orthopedic bone fixation plate 160, 260, 360, 460, 560, 660, 760, 860 at varying angles relative to a plate surface 160a, 260a, 360a, 460a, 560a, 660a, 860a and at varying radial directions relative to a center axis 160b, 260b, 360b, 460b, 560b, 660b, 760b, 860b of the bone fixation plate hole 160c, 260c, 360c, 460c, 560c, 660c, 760c, 860c.

Referring to FIGS. 1-6, the sliding plate variable angle locking mechanism 10 of the first preferred embodiment includes first and second sliding plates 100, 110 that cooperate with one or more rotating plates 120 to provide an angularly adjustable hole into which the bone fixation screw 130 may be secured. The sliding plates 100, 110 and the one or more rotating plates 120 are initially arranged in such a manner that centers 105a, 115a, 125a of screw holes 105, 115, 125 of the sliding plates 100, 110 and the rotating plate 120, respectively, form a sliding plate longitudinal axis 106 that is parallel to the central axis 160b of the corresponding bone fixation plate hole 160c. When the bone fixation screw 130 is secured into the sliding plate variable angle locking mechanism 10 of the first preferred embodiment, the screw 130 may be fixed at an angle orthogonal to the bone plate surface 160a such that the long axis of the screw 130 is in line with the centers 105a, 115a, 125a of the sliding plates 100, 110 and rotating plate 120, which is in line with the center axis 160b of the bone fixation plate hole 160c.

Figure 2A:
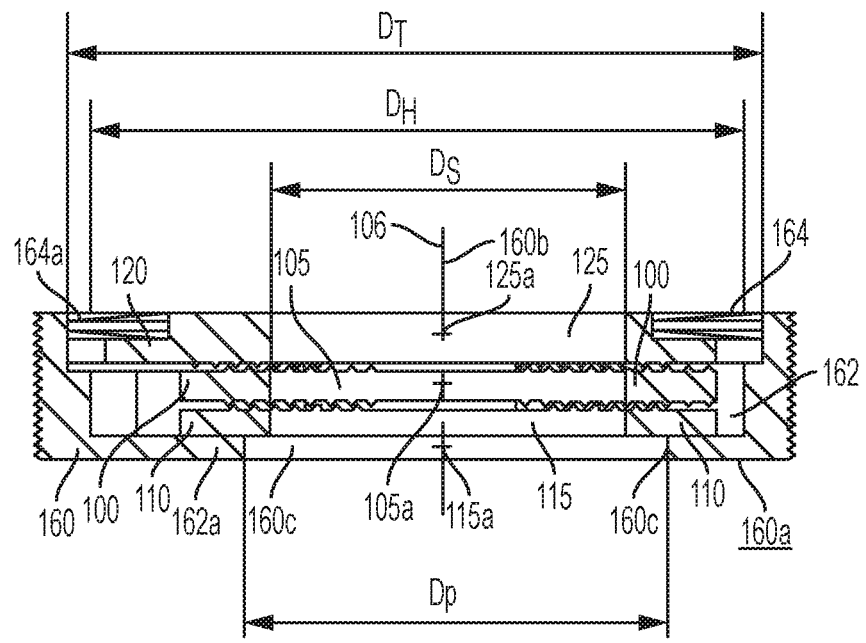
FIG. 2a is a cross-sectional view of the sliding plate variable angle locking mechanism of FIG. 1, taken along line X-X of FIG. 1 wherein the sliding plates are positioned such that an axis passing through each hole center is parallel to a line orthogonal to a bone fixation plate surface of the bone plate.
Figure 2B:
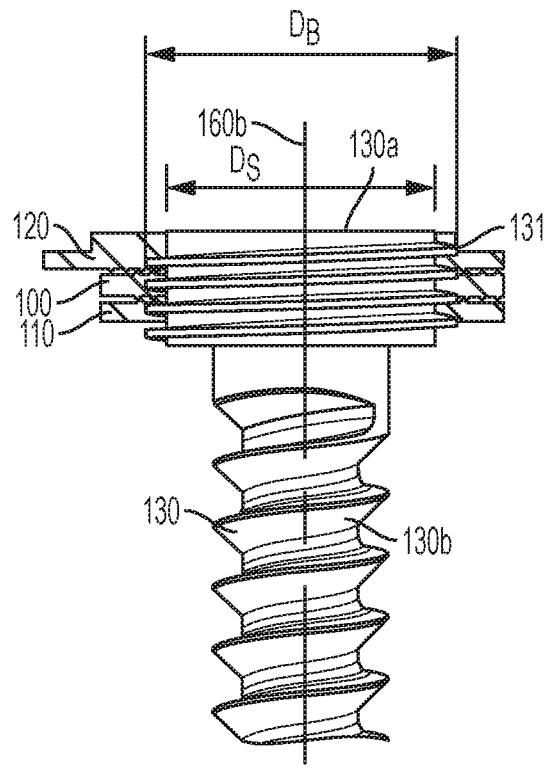
FIG. 2b is a partial cross-sectional view corresponding to FIG. 2a with the bone plate removed for clarity and a bone fixation screw in a locked position with its axis parallel with the central axis of the bone fixation plate hole (not shown) and the axis passing through each hole center of the sliding plates.
Figure 3A:
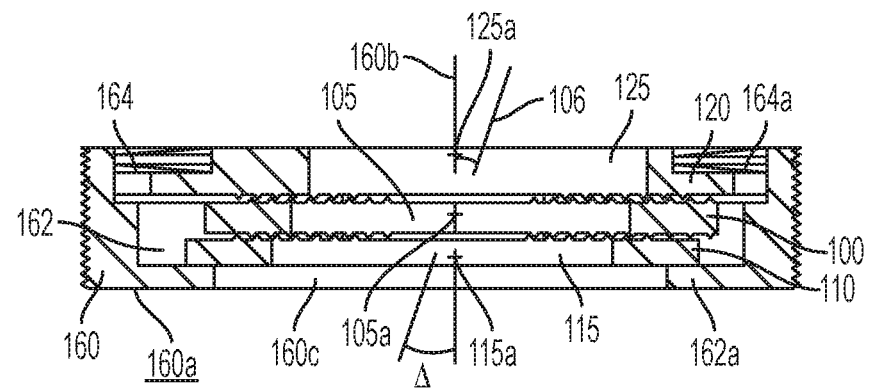
FIG. 3a is a cross-sectional view of the sliding plate variable angle locking mechanism of FIG. 1, taken along line X-X of FIG. 1, wherein sliding plates and a rotating plate are positioned such that the axis passing through each hole center is at an angle offset from the central axis of the bone fixation plate surface of the bone plate.
Figure 3B:
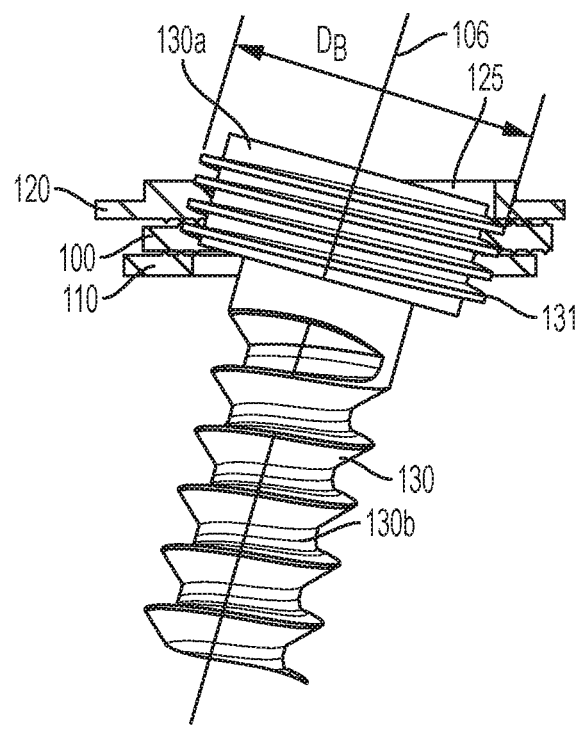
FIG. 3b is a partial cross-sectional view corresponding to FIG. 3a with the bone plate removed for clarity and a bone fixation screw in a locked position with its axis at an angle offset from the central axis of the bone fixation plate hole (not shown)

In the first preferred embodiment, the center 125a of the rotating plate 120 is at least slightly offset from a center of the perimeter of the rotating plate 120, such that the hole 125 of the rotating plate 120 is positioned at least slightly off-center from the perimeter of the rotating plate 120. The off-center positioning of the hole 125 of the rotating plate 120 can be seen in FIGS. 2a and 3a, wherein additional material of the rotating plate 120 is located on the left-side of the cross-sectional view when compared to the right-side portion of the rotating plate 120. The offset of the hole 125 and center 125a of the rotating plate 120 is designed to allow greater offset angles Δ without having to have a larger hole in the rotating plate 120 or expanding the size of the hole 125 in the rotating plate 120. The rotating plate 120 and the first and second sliding plates 100, 110 may be positioned such that the screw 130 is orthogonal to the bone plate 160, the first and second sliding plates 100, 110 and the rotating plate 120 or substantially parallel relative to the center axis 160b of the plate 160 (FIG. 2b). To create the offset angle Δ or pivot the bone screw 130 out of this orthogonal position, the sliding plates 100, 110 only have to translate to the left when considering the view of FIG. 2a. If the operator wants the offset angle Δ to the right, the operator simply rotates the rotating plate one hundred eighty degrees (180°) about the center axis 160b of the bone fixation plate 160. That is, in this configuration, the rotating plate 120 only includes a single opening 142 between the sliding guides 140 and the sliding guides 140 extend around the perimeter of the rotating plate 120 approximately two hundred seventy degrees (270°) or about three-fourths of the way around the perimeter of the rotating plate 120. The sliding guides 140 may also be configured to extend only from two sides of the rotating plate 120, thereby defining the pair of openings 142 on opposing sides of the rotating plate 120 through which the first and second sliding plates 100, 110 may slide in the assembled configuration. In the first preferred embodiment, the bone screw 130 preferably only pivots in the direction toward and away from the opening 142 between the ends of the sliding guides 140 or generally along a sliding axis 143 of the rotating plate 120. If the hole 125 in the rotating plate 120 is alternatively positioned in the symmetrical center of the perimeter of the rotating plate 120, the geometry of the hole 125 of the rotating plate 120 is preferably, slightly bigger to accommodate the sliding plates 100, 110 moving in both directions, as opposed to generally only in the direction toward the opening 142 in the assembled configuration.

The bone plate 160, the sliding plates 100, 110, the rotating plate 120 and the bone screw 130 are each preferably constructed of a relatively rigid and durable biocompatible material, such as stainless steel, iron steel, titanium or titanium alloy. Additionally or alternatively, non-metal biocompatible materials may also be utilized such as polymers, elastomers, resins, ceramics, and composites thereof, such as polyether ether ketone ("PEEK"), ultra-high-molecular-weight polyethylene (UHMWPE) and other related polymeric materials. These components may also be constructed of nearly any material that will not cause any adverse chemical or immunological reactions after being implanted into a patient's body that is able to take on the general size and shape of these components and withstand the normal operating conditions of these components. These components may also be constructed of a biocompatible metal-synthetic hybrid material or entirely from a biocompatible synthetic material. Examples of biocompatible metals that may be utilized to construct the components of the sliding late variable angle locking mechanisms 10, 20, 30, 40, 50, 60, 70 of the preferred inventions include titanium, stainless steel, zirconium, tantalum, cobalt, chromium, nickel and alloys thereof. Examples of biocompatible synthetic materials that may be utilized to construct the components of the sliding late variable angle locking mechanisms 10, 20, 30, 40, 50, 60, 70 of the preferred inventions include polymers, elastomers, resins, plastics, carbon graphite and composites thereof.

In the first preferred embodiment, the sliding plates 100, 110 and the rotating plate 120 have a sliding plate hole diameter $D_S$ that are substantially the same, but are not so limited and the sliding plate hole diameter $D_S$ may be different for each of the sliding plates 100, 110 and the rotating plate 120. The sliding plate hole diameters $D_S$ for each of the sliding plates 100, 110 and the rotating plate 120 are substantially the same in the first preferred embodiment such that the bone fixation screw 130 makes internal threads 130a in the sliding plates 100, 110 and the rotating plate 120, when the bone fixation screw 130 is driven into the holes 105, 115, 125, as will be described in greater detail below. The plate hole 160c is positioned at the lower portion of the plate 160 adjacent the bone plate surface 160a and has a plate hole diameter $D_P$. The plate hole diameter $D_P$ is greater than the sliding plate hole diameters $D_S$ in the first preferred embodiment, such that the bone screw 130 generally does not come into contact with the edges of the plate hole 160c when the bone screw 130 is mounted to the plate 160. The bone plate 160 preferably has a plate cavity 180 formed therein that includes the plate hole 160c, a shelf hole 162 and a threaded hole 164 with the shelf hole 162 positioned between the plate hole 160c and the threaded hole 164. The shelf hole 162 has a shelf hole diameter $D_H$ that is greater than the plate hold diameter $D_P$, thereby forming a shelf 162a in the plate 160 near the bottom of the plate cavity 180 proximate the bone plate surface 160a. The shelf 162a supports the sliding plates 100, 110 and the rotating plate 120 in the plate cavity 180 in an assembled configuration. The threaded hole 164 preferably has a threaded hole diameter $D_T$ that is greater than the shelf hold diameter $D_H$. In the first preferred embodiment, the sliding plates 100, 110 and the rotating plate 120 are positioned within the plate cavity 180 and are supported by the shelf 162a in the assembled configuration.

Referring to FIGS. 2a-3c in the first preferred embodiment, the first and second sliding plates 100, 110, cooperating with the rotating plate 120, may be arranged in such a manner that the centers 105a, 115a, 125a of the sliding and rotating plate screw holes 105, 115, 125 form the sliding plate longitudinal axis 106 positioned at an offset angle Δ relative to the center axis 160b of the corresponding bone fixation plate hole 160c. When the bone fixation screw 130 is secured into the sliding plate variable angle locking mechanism 10 at this offset angle Δ, the screw 130 is fixed at the angle offset angle Δ relative to the plate surface 160a in the locked configuration.

The sliding plate variable angle locking mechanism 10 is not limited to including only the first and second sliding plates 100, 110 and may include additional sliding plates (not shown) in addition to the first and second sliding plates 100, 110, depending on user or designer preferences, design factors or for other similar reasons. The first and second sliding plates 100, 110 and the additional sliding plates are preferably stacked in the plate cavity 180 in the assembled configuration and functions similarly to the function of the first and second sliding plates 100, 110.

The positioning of the sliding plates 100, 110 and the rotating plate 120 relative to each other is adjustable as the desired offset angle Δ is initially set. In an unlocked or relaxed configuration, the sliding plates 100, 110 and the rotating plate 120 are free to translate along a plane parallel to their upper and/or lower surfaces or generally parallel to the bone plate surface 160a. The sliding plates 100, 110 and the rotating plate 120 are preferably guided in their sliding movement along the top surface of the shelf 162a and are bounded in the plate cavity 180 by the walls of the shelf hole 162 and the threaded hole 164. Once the desired offset angle Δ for the bone fixation screw 130 is set, each of the sliding plates 100, 110 and the rotating plate 120 are securely fixed in the offset or angled position relative to one another and to the rotating plate 120, such that their centers 105a, 115a, 125a are aligned on the sliding plate longitudinal axis at the offset angle Δ.

Referring to FIGS. 1-5, the rotating plate 120 includes sliding plate guides 140 that extend below its lower surface and along sides of the first and second sliding plates 100, 110 in the mounted configuration and in the plate cavity 180. The sliding plate guides 140 restrict translation of the sliding plates 100, 110, preferably to a single degree of freedom within the plane parallel to their upper and/or lower surfaces relative to the rotating plate 120 or generally linearly through openings 142 between the sliding plate guides 140.

The sliding plate variable angle locking mechanism 10 of the first preferred embodiment also includes a locking ring 150 with external threads 150a that mate with cavity threads 164a of the threaded hole 164 such that the locking ring 150 is removable from the bone plate 160, but is not so limited.

The locking ring 150 may be blocked from being removed from the plate cavity 180 by a feature of the bone plate 160 or the plate cavity 180. In addition, the sliding plate variable angle locking mechanism 10 may be configured such that the locking ring 150 may be swaged or otherwise secured to the bone plate 160 through use of a separate tool (not shown) that engages the locking ring 150 to the bone plate 160 and applies compression forces to the rotating plate 120 and the first and second sliding plates 100, 110 onto the shelf 162a once the position of the rotating plate 120 and the first and second sliding plates 100, 110 is established, as will be described in further detail below. The locking ring 150 also preferably mates with the rotating plate 120 in the mounted configuration such that the rotating plate 120 can rotate about its center 125a within the cavity 180 when the locking ring 150 is not fully tightened. Because the sliding guides 140 of the rotating plate 120 generally maintain the rotational alignment of the first and second sliding plates 100, 110 relative to that of the rotating plate 120, the screw holes 105, 115 of the sliding plates 100, 110 substantially only translate through the openings 142 between the sliding guides 140. The sliding plates 100, 110 also preferably includes linear side guides 100a, 110a that are slidable along the sliding guides 140 to substantially guide the sliding plates 100, 110 linearly relative to the rotating plate 120 for translation in the one degree of freedom described above. Accordingly, in the first preferred embodiment, regardless of the orientation of the rotating plate 120 about the center axis 160b, the sliding plates 100 and 110 generally translate along a line extending radially from the center 125a of the hole 125 of the rotating plate 120 relative to the center axis 160b of the plate hole 160c in the mounted configuration.

Rotation of the rotating plate 120 relative to the locking ring 150 and the bone fixation plate 160 within the plate cavity 180 will reorient the position of the rotating plate screw hole 125 radially about the central axis of the locking ring 150. Additionally, the sliding plates 100, 110 will correspondingly reorient about the center axis 160b due to the influence of the sliding plate guides 140. Upon establishing a desired bone fixation offset angle Δ relative to the bone fixation plate surface 160a and the center axis 160b by appropriately translating the sliding plates 100, 110 relative to each other and the rotating plate 120, the resulting variability of potential orientations of the bone fixation screw 130 generated by the combination of rotational orientation of the rotating plate 129 and translational motion of the sliding plates 100, 110 describes a conical area beneath the bone plate surface 160a of the bone fixation plate 160. Thus, the variable angle locking mechanism 10 of the first preferred embodiment provides a multitude of bone fixation screw orientations or offset angles Δ relative to the bone fixation plate 160. The translational movement of the sliding plates 100, 110 and the rotating plate 120 may be urged into numerous offset angles Δ and orientations relative to the center axis 160b and the bone plate surface 160a by inserting the bone screw 130 relatively loosely therein and aiming the bone screw 130, utilizing an external tool targeting tool (not shown) that orients the sliding plates 100, 110 and the rotating plate 120 or during initial surgical procedures, such as drilling a hole in the bone, tapping a bone hole or aiming the drill.

The rotating plate 120 and the sliding plates 100, 110 are preferably designed and configured such that the rotating plate 120 is rotatable within the generally cylindrical plate cavity 180, while the first and second sliding plates 100, 110 are generally not rotatable relative to the rotating plate 120, but do rotate in the plate cavity 180 when the rotating plate 120 rotates in the plate cavity 180. The sliding guides 140 of the rotating plate 120 generally limit rotatability of the first and second sliding plates 100, 110 relative to the rotating plate 120 in the assembled configuration and also guide the sliding or lateral movement of the first and second sliding plates 100, 110 relative to the rotating plate 120. The sliding plates 100, 110 are guided in their sliding or lateral movement to facilitate the offset angle Δ along a sliding axis 143 that is generally perpendicular relative to the center axis 160b of the bone plate 160 and is generally parallel to the linear side guides 100a, 110a of the first and second sliding plates 100, 110. In operation, the user arranges the rotating plate 120 with the opening 142 facing in the direction of the desired target direction of the bone screw 130. The bone screw 130 or an alignment tool is inserted through the holes 105, 115, 125 of the first and second sliding plates 100, 110 and the rotating plate 120 to arrange the centers 105a, 115a, 125a along the desired sliding plate longitudinal axis 106 to define the desired offset angle Δ. The bone screw 130 is then screwed into the bone and the head 130a is driven into the rotating plate 120 and into the first and second sliding plates 100, 110 to form the internal threads 170 on the inner surfaces of the first and second sliding plates 100, 110 and the rotating plate 120. The rotating plate 120 may include a visual indicator (not shown) on its top surface or any surface visible to the operator to indicate the direction or orientation of the opening 142 for targeting purposes, but is not so limited and may be configured without the indicator.

In the first preferred embodiment, the locking ring 150 has a locking ring hole diameter 150d through which the bone screw 130 may extend for securing the bone plate 160 to the bone. The locking ring hole 150d defines a locking ring hole diameter $D_L$ that is greater than the sliding plate hole diameter $D_S$. The bone screw 130 is preferably able to extend through the locking ring hole 150d without contacting the locking ring 150. When the bone screw 130 extends into the plate cavity 180 in the assembled configuration, the bone screw 130 preferably contacts only the first and second sliding plates 100, 110 and the rotating plate 120 and forms internal threads 170 in the first and second sliding plates 100, 110 and the rotating plate 120 to create a strong bond between the first and second sliding plates 100, 110 and the rotating plate 120 with the bone screw 130.

For the purpose of establishing the rigidity required for securing the bone fixation screw 130 to the bone fixation plate 160, the sliding plates 100, 110 are translationally fixed in place relative to each other and to the rotating plate 120. In addition, the rotating plate 120 is preferably, substantially rotationally fixed in place relative to the locking ring 150. This is preferably achieved in a number of ways by incorporating the force of friction to generally prevent relative motion between any two surfaces of the herein described variable angle locking mechanism 10, including the sliding plates 100, 110 relative to the shelf 162a, the sliding plates 100, 110 relative to each other and the rotating plate 120 relative to the sliding plates 100, 110. Frictional force is the product of the coefficient of friction corresponding to the material properties of the associated contact surfaces and a force vector acting normal to the surface interface. Given a constant coefficient of friction, frictional force can be increased in proportion to increased force acting on the surfaces. Sufficient normal force in combination with appropriate materials, such that the coefficient of friction is conducive to generating sufficient friction, will provide the rigidity required to secure the bone fixation screw 130 to the bone fixation plate 160 in a manner suitable for orthopedic applications.

Referring to FIGS. 4 and 5, a normal force can be imparted by the locking ring 150 onto the rotating plate 120, through the intermediate sliding plates 100, 110, and reacted to oppositely by the bone fixation plate hole flange 165 on the shelf 162a in the locked configuration. Thus, frictional forces resistant to both linear motion of the sliding plates 100, 110 and rotational motion of the rotating plate 120 will be established. The upper surface of the bone fixation plate flange 165 or shelf 162a reacting with the lower surface of first sliding plate 100 will produce frictional forces that oppose both translation and rotation of first sliding plate 100 in the locked configuration. The upper surface of first sliding plate 100 preferably reacts with the lower surface of second sliding plate 110 to produce a frictional force that opposes translation between the first and second sliding plates 100, 110. The upper surface of second sliding plate 110 preferably reacts with the lower surface of the rotating plate 120 to produce a frictional force that opposes translation of the second sliding plate 110 in the locked position. The upper surface of rotating plate 120 preferably reacts with the lower surface of the locking ring 150 to produce a frictional force that opposes rotation of the rotating plate 120 in the locked position or configuration.

Figure 6:
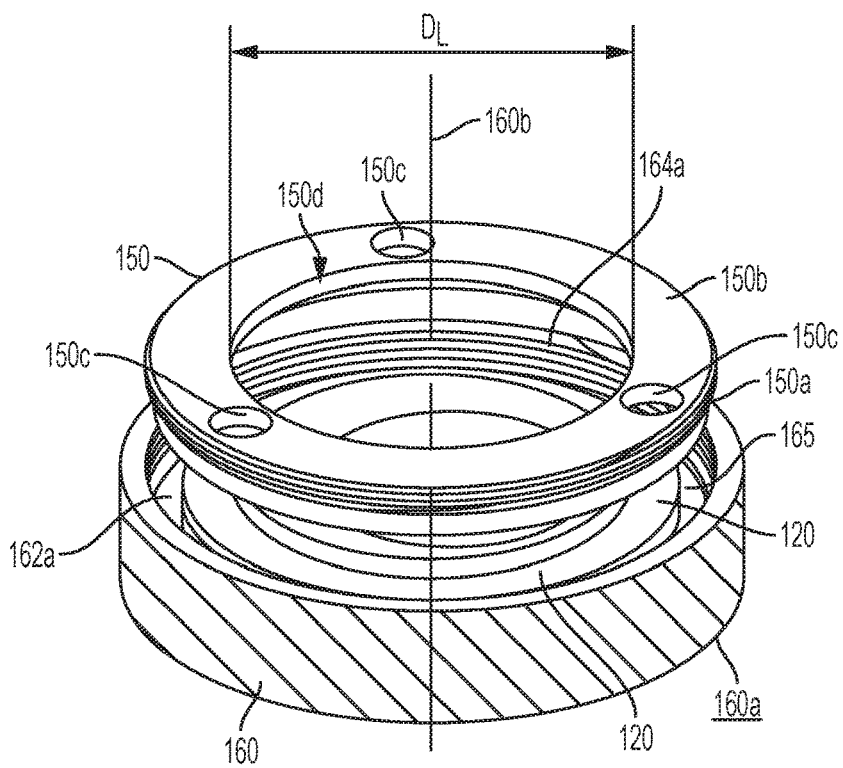
FIG. 6 is a magnified, partial cross-sectional, partially exploded top perspective view of the sliding plate variable angle locking mechanism of FIG. 1, showing the locking ring partially exploded from the sliding plates and the bone plate.

The normal force imparted on the upper surface of the rotating plate 120 by the locking ring 150 can be achieved by various mechanisms or features for generating force. FIG. 6 shows the locking ring 150 with the machined external threads 150a encircling a ring collar 150b of the locking ring 150. The cavity threads 164a in the upper circumference of the plate cavity 180 of the bone fixation plate 160 correspond to the external threads 150a of the locking ring 150 such that the locking ring 150 can be screwed into the cavity 180. Circular features 150c, or similar provisions, in the upper surface of the locking ring 150 preferably provide a mechanism or feature for a tool (not shown) to engage and impart a torque onto the locking ring 150. The downward translation of the locking ring 150 as it is screwed into the cavity 180 of the bone fixation plate 160 will eventually place the lower surface of the locking ring 150 in contact with the upper surface of the rotating plate 120. Continued rotation of the locking ring 150 into the cavity 180 imparts a normal force onto the rotating plate 120, thereby creating the desired frictional force among the sliding plates 100, 110 of the first preferred variable angle locking mechanism components and, thus, lock the first preferred mechanism 10 in the locked position for rigidly securing a bone fixation screw 130 relative to the plate 160.

Figure 14:
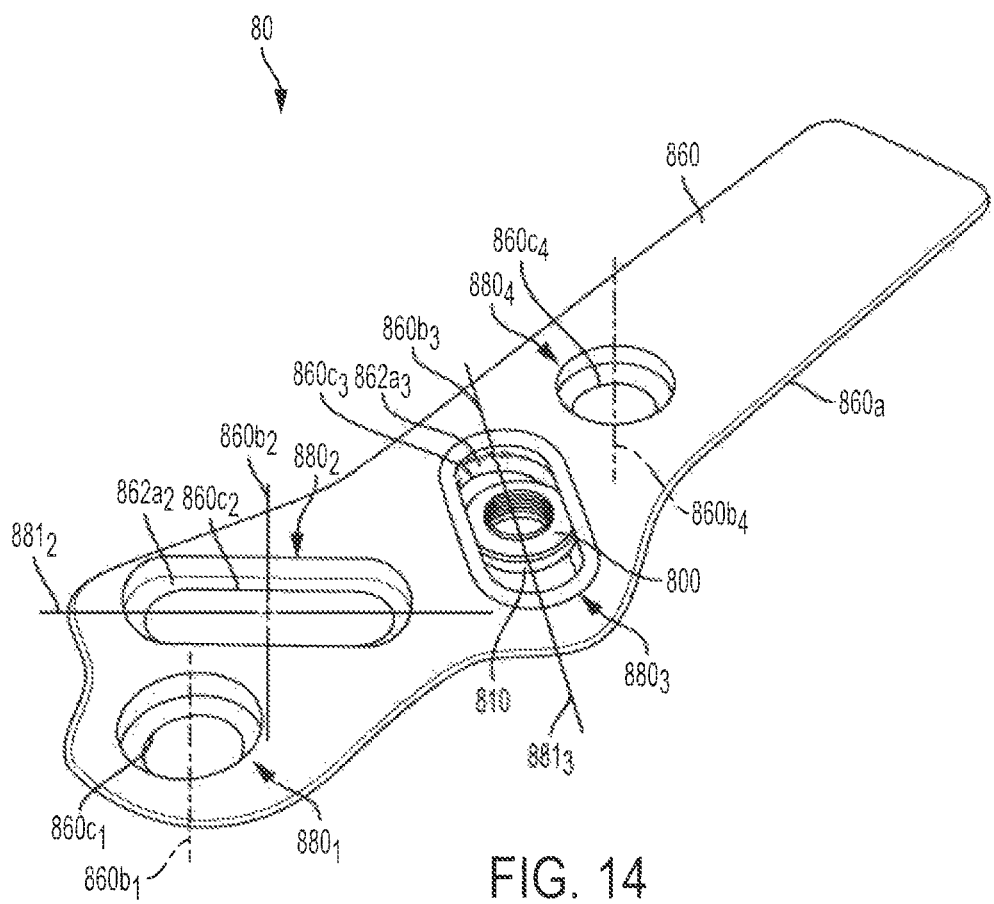
FIG. 14 is a top perspective view of an eighth preferred embodiment of a sliding plate variable angle locking mechanism.

Referring to FIG. 14, an eighth preferred sliding plate variable angle locking mechanism 80 has a similar construction compared to the first preferred sliding plate variable angle locking mechanism 10 and like reference numbers are utilized to identify like features of the eighth preferred sliding plate variable angle locking mechanism 80 with a number "8" prefix replacing the "1" prefix to distinguish the features of the sliding plate variable angle locking mechanism 10 of the first preferred embodiment from the sliding plate variable angle locking mechanism 80 of the eighth preferred embodiment.

The sliding plate variable angle locking mechanism 80 of the eighth preferred embodiment includes first, second, third and fourth plate cavities $880_1$, $880_2$, $880_3$, $880_4$ in the bone plate 860 with the first and fourth plate cavities $880_1$, $880_4$ having a construction and configuration that is nearly identical to any of the above-described first through seventh preferred embodiments. The second and fourth plate cavities $880_2$, $880_3$ have slot axes $881_2$, $881_3$ that extend substantially perpendicular to the center axes $860b_2$, $860b_3$ and generally parallel to the bone plate surface 860a. The second and fourth plate cavities $8802$, $8803$ are elongated and the slot axes $881_2$, $881_3$ extend generally parallel relative to the length of the slots. In any of the first through seventh preferred embodiments of the sliding plate variable angle locking mechanisms 10, 20, 30, 40, 50, 60, 70, described above, whereby the bone fixation screw 130 with the threads 131 on the head 130a are designed to tap into and engage the sliding plates 100, 110 with or without the rotating plates 120 and the locking rings 150 imparts additional locking forces between the bone fixation screw 130 and the bone fixation plates 160, 260, 360, 460, 560, 660, 760, the sliding plates 100, 110 with or without the rotating plate 120 may be configured to translate along a slot having a configuration similar to the second and third plate cavities $880_2$, $880_3$ of the eighth preferred embodiment The bone plate 860 of the eighth preferred embodiment includes the first, second, third and fourth plate cavities $860_1$, $860_2$, $860_3$, $860_4$ wherein the second and third plate cavities $860_2$, $860_3$ include the described slots having the slot axes $881_2$, $881_3$ that extend generally parallel to the bone plate surface 860a and are generally perpendicular relative to the center axes $860b_2$, $860b_3$ of the respective second and third plate cavities $860_2$, $860_3$. The second and third plate cavities $880_2$, $880_3$ include shelfs $862a_2$, $862a_3$ with rounded ends and longitudinal sides that extend generally parallel to the second and third slot axes $881_2$, $881_3$, respectively. The locking features, such as the first and second sliding plates 100, 110 and the rotating plate 120 may be mounted within the second and third plate cavities $860_2$, $860_3$. Utilizing the second and third plate cavities $860_2$, $860_3$ rather than the generally circular or cylindrical-type first and second plate cavities $860_1$, $860_4$, the sliding plates 100, 110 with or without the rotating plate 120 can be moved laterally within the second and third plate cavities $860_2$, $860_3$, substantially parallel to the second and third slot axes $881_2$, $881_3$, respectively, to not only provide a conical range of angulations for the bone screw 130 relative to the bone fixation plate 860, but also allow a variety of positions of the screw angulation cone along second and third slot axes $881_2$, $881_3$, respectively. This flexibility provides a surgeon who not only desires to fix the bone screw 130 at the offset angle Δ relative to the plate 860, but also allows the surgeon to position the bone screw 130 at various locations within the plate boundary. The second and third plate cavities $860_2$, $860_3$ can be linear, as is shown in the eighth preferred embodiment, but may alternatively be curvilinear to provide a multitude of options for locating the bone screw 130 within the plate 860.

In operation, the assembled sliding plate variable angle locking mechanism 10 of the first preferred embodiment is placed on a bone and the surgeon determines a desired location for the plate hole 160c. The surgeon also preferably elects a preferred orientation of the bone fixation screw 130 relative to the plate 160. The plate 160 preferably includes multiple plate holes 160c and plate cavities 180, but the single plate hole 160c and cavity 180 is shown here for simplicity and clarity. The rotating plate 120 is pivoted such that the openings 142 are aligned with a direction selected by the surgeon to orient the bone screw 130.

The bone screw 130 is screwed into the bone at the desired offset angle Δ until a head 130a of the bone screw 130 engages the rotating plate 120. Head threads 131 on the head 130a engage and cut the internal threads 170 into the rotating plate 120, the first sliding plate 100 and the second sliding plate 110 as the screw 130 continues to drive into the bone. The internal threads 170 are formed in the rotating plate 120 and the first and second sliding plates 100, 110 such that the screw 130 is oriented at the desired offset angle Δ. The head threads 131 are preferably configured to form the internal threads 170, such as by being constructed of a material having a greater hardness than the hardness of the rotating plate 120 and the first and second sliding plates 100, 110. When the bone screw 130 is positioned as desired, the locking ring 150 is tightened to lock the bone screw 130 relative to the plate 160 by friction forces, as was described above. The locking ring 150 may alternatively be tightened, thereby locking the rotating plate 120 and first and second sliding plates 100, 110 after the offset angle Δ is set, but before the screw 130 is driven into the bone. The bone screw 130, the plate hole 160c, the first and second sliding plates 100, 110, the rotating plate 120 and the locking ring 150 are preferably constructed such that the bone screw 130 and, particularly the head 130a and head threads 131 generally do not contact or cut into the bone plate 160, particularly the plate hole 160c or the locking ring 150 in a mounted configuration, locked configuration (FIGS. 2b, 3b and 5) or during insertion of the bone screw 130 into the plate cavity 180. These components are not so limited and the bone screw 130 may contact the plate hole 160c or locking ring 150, particularly at extreme or relatively large offset angles Δ.

In the first preferred embodiment, the head threads 131 define a bone screw head diameter $D_B$ that is greater than sliding plate hole diameter $D_S$. Accordingly, when the head 130a of the bone screw 130 is driven into the first and second sliding plates 100, 110 and the rotating plate 120, the larger bone screw head diameter $D_B$ requires the internal threads 170 to be cut into the first and second sliding plates 100, 110 and the rotating plate 120, which each preferably have the smaller sliding plate hole diameter $D_S$ in their central holes 105, 115, 125.

Figure 7:
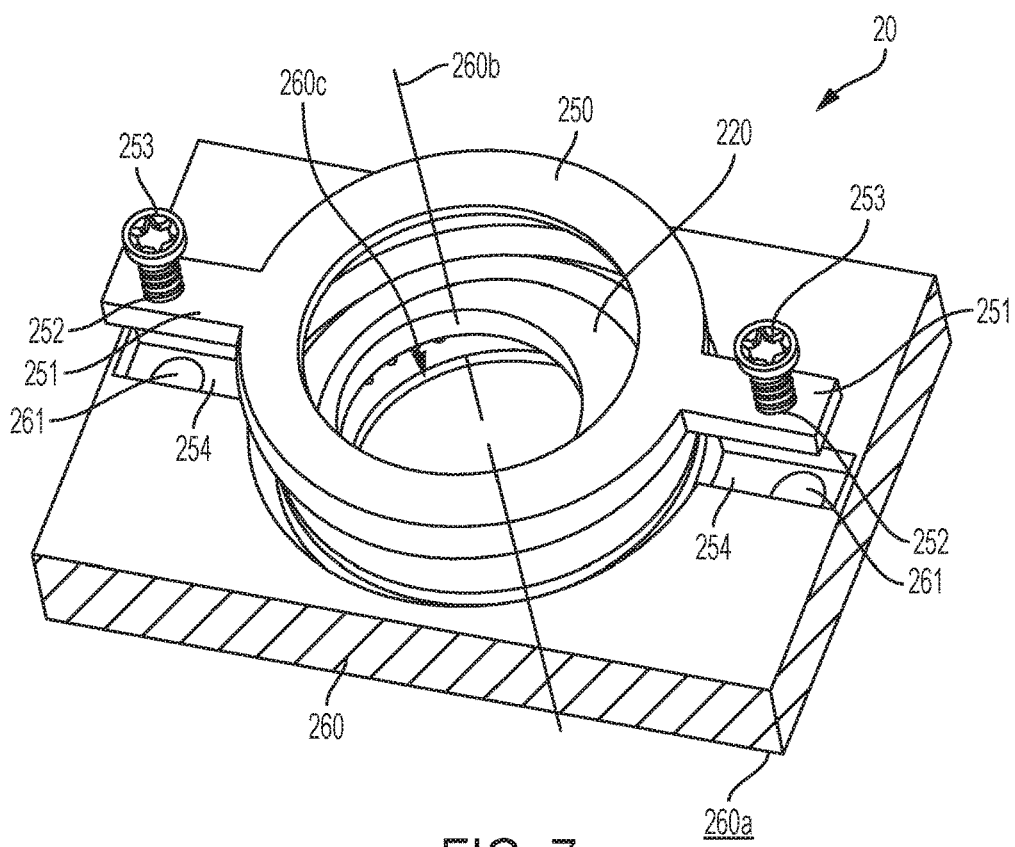
FIG. 7 is partial cross-sectional, partially exploded, top perspective view of a second preferred embodiment of a sliding plate variable angle locking mechanism, showing a locking ring partially exploded from a bone fixation plate.

Referring to FIG. 7, a second preferred sliding plate variable angle locking mechanism 20 has a similar construction compared to the first preferred sliding plate variable angle locking mechanism 10 and like reference numbers are utilized to identify like features of the second preferred sliding plate variable angle locking mechanism 20 with a number "2" prefix replacing the "1" prefix to distinguish the features of the sliding plate variable angle locking mechanism 10 of the first preferred embodiment from the sliding plate variable angle locking mechanism 20 of the second preferred embodiment.

In the second preferred embodiment, a normal force may be applied onto the rotating plate 220 by driving tightening screws 252 into holes in tabs 251 extending from sides of the locking ring 250. The tabs 251 preferably protrude radially from the circumference of the locking ring 250 and two tabs 251 are shown in the second preferred embodiment. The second preferred embodiment is not limited to having the two tabs 251 and may include additional tabs 251. The tabs 251 include holes 252 located therein for the insertion of a screw 253 such that the screw 253 passes through the tab 251 and is capable of screwing into a corresponding receiving hole 261 in the bone fixation plate 260. Recesses 254 are preferably provided in the bone fixation plate 260 corresponding to and beneath the locking ring tabs 251 such that the locking ring 250 will not be obstructed by the bone fixation plate 260 during downward translation onto the rotating plate 220. As described in the first preferred embodiment, downward translation of the locking ring 250 as screws 253 are screwed into the bone fixation plate receiving holes 261 places the lower surface of the locking ring 250 in contact with the upper surface of the rotating plate 220. Continued tightening of the screws 253 into the receiving holes 261 imparts increasing normal forces onto the rotating plate 220, thereby creating the desired frictional force among the sliding plate variable angle locking mechanism 20 components and, thus, locking the mechanism 20 in the locked position for rigidly securing the bone fixation screw 130 and setting the desired offset angle Δ relative to the plate 260.

Referring to FIGS. 8a-9b, a third preferred sliding plate variable angle locking mechanism 30 has a similar construction compared to the first preferred sliding plate variable angle locking mechanism 10 and like reference numbers are utilized to identify like features of the third preferred sliding plate variable angle locking mechanism 30 with a number "3" prefix replacing the "1" prefix to distinguish the features of the sliding plate variable angle locking mechanism 10 of the first preferred embodiment from the sliding plate variable angle locking mechanism 30 of the third preferred embodiment.

Figure 8A:
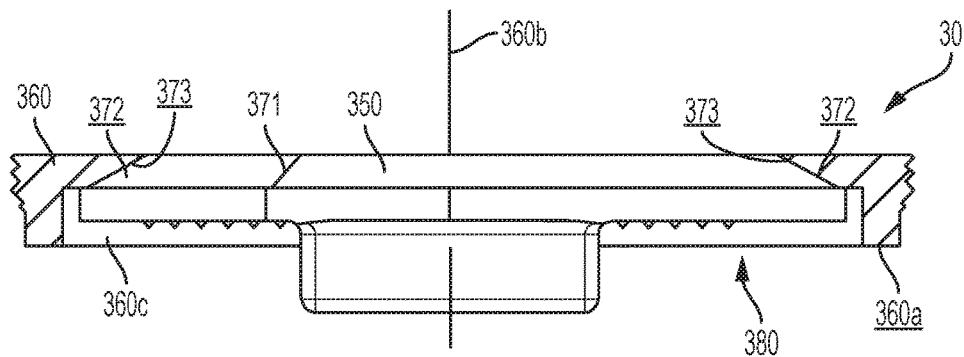
FIG. 8a is a partial cross-sectional, side elevational view of a third preferred embodiment of a sliding plate variable angle locking mechanism, showing a chamfered perimeter of a bone plate for engagement with a chamfered locking ring in a locked configuration or position, wherein the rotating plate is also sectioned into a plurality of segments allowing it to expand with the insertion of a bone fixation screw.
Figure 8B:
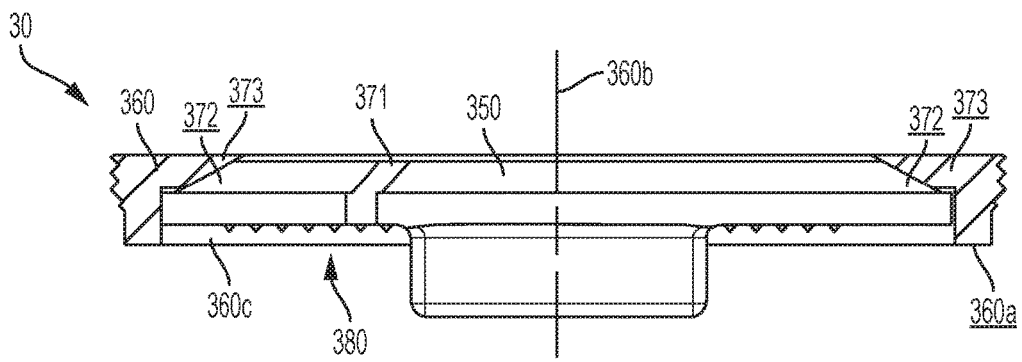
FIG. 8b a partial cross-sectional, side elevational view of the sliding plate variable angle locking mechanism of FIG. 8b, wherein the locking ring is in a relaxed or unlocked configuration.
Figure 9A:
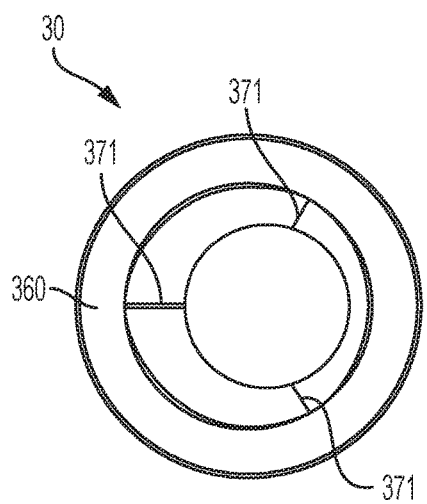
Figure 9B:
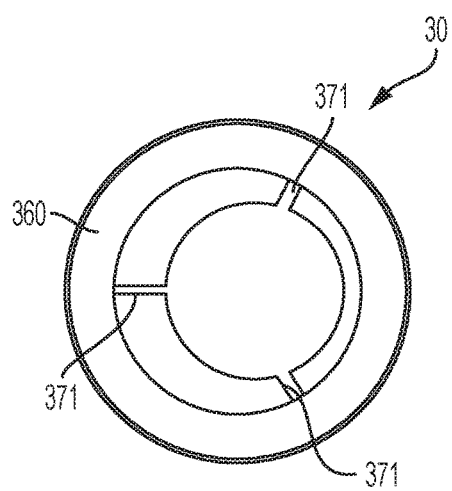
FIG. 9b is a top plan view of the sliding plate variable angle locking mechanism of FIG. 8b.

The third preferred variable angle locking mechanism 30 includes only the rotating plate 320 with a plurality of sections that are movably or crushably separated radially from the center of the rotating plate 320, thereby forming joints 371. The rotating plate 320 is positioned in the plate cavity 380, which is formed in the plate 360 with its greatest diameter adjacent the bone plate surface 360a and a narrower diameter proximate a top of the plate 360. As shown in FIG. 8a, the upper perimeter of the rotating plate 320 has an inwardly sloping surface 372 forming a chamfer around its circumference and the cavity 380 has a corresponding sloping surface 373 facing toward the plate hole 360c. It should be understood that the sloping surface 373 could be formed on a separate component that is secured or fixed to the bone plate 360, as opposed to forming the sloping surface 373 direction in the bone plate 360, thereby permitting removal and replacement of the separate component in the bone plate 360 and engagement of a component having different feature, such as a different angle on the sloping surface 373. This separate component would provide additional flexibility in that it can be adjusted for appropriate spacing in relation to the upper surface of the rotating plate 350. The rotating plate sections are configured in the third preferred embodiment such that there is preferably no gap between the sections at any of the joints 371. In this configuration, the rotating plate 350 is positioned vertically such that it would not impart any downward force onto any sliding plates (not shown) that are positioned below the rotating plate 350, thereby creating no additional frictional forces in the sliding plate variable angle locking mechanism 30. The bone fixation screw 130 that includes the threaded head 130a of appropriate diameter is inserted into the bone fixation plate hole 360c to a point at which the head 130a engages with the rotating plate 350. Further insertion and tapping of the screw head 130a threads into the rotating plate 350 and imparts an outward radial force on the rotating plate sections. The configurations of FIGS. 8a and 9a show the joints 371 in a collapsed and locked configuration and the configurations of FIGS. 8b and 9b show the joints 371 in a relaxed and unlocked configuration. The joints 371 are formed due to a displacement of each of the rotating plate sections radially outward from the center of the rotating plate 350. In this configuration, the sloping surface 373 of the bone plate 360 contacts the sloping surface of the rotating plate 350 such that continued radial displacement of the rotating plate sections forces a downward displacement relative to the slope of the sloping surface 373. The downward displacement of the rotating plate sections imparts a downward force onto the sliding plates below, thereby creating sufficient frictional force in the sliding plate variable angle locking mechanism 30 to rigidly secure the bone fixation screw 130.

It can be understood that there are a number of various means for imparting downward force onto the upper surface of the rotating plates 120, 220, 320 and application herein is not limited to the above examples. Locking pins with wedge or cam shaped heads could be used along the circumference of a circular locking ring to force it downward or other similar features or mechanisms may be employed.

Figure 10:
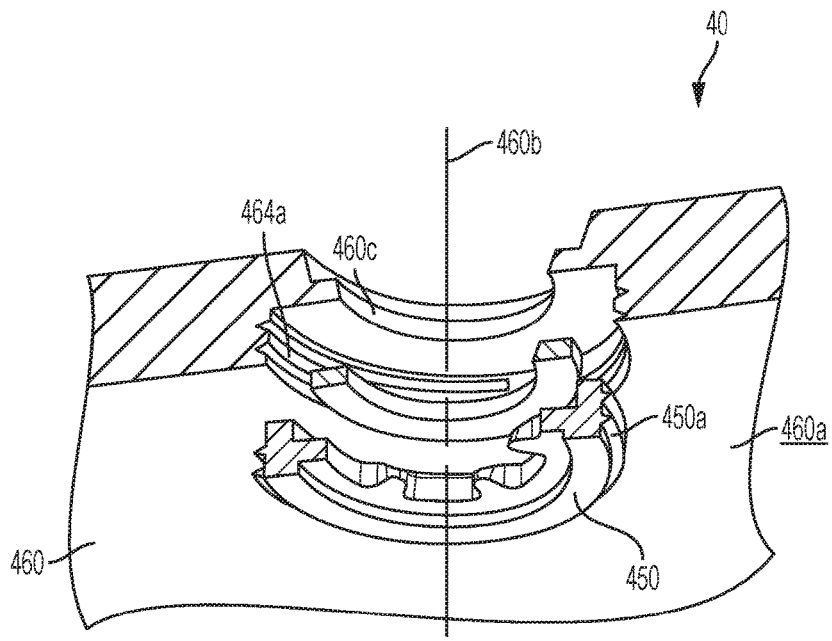
FIG. 10 is a partial cross-sectional, exploded, bottom perspective view of a fourth preferred embodiment of a sliding plate variable angle locking mechanism, whereby a locking ring is positioned proximate a lower or bone contacting surface of a bone fixation plate hole, wherein the locking ring has bone fixation screw engagement features that transfer rotational force of a bone fixation screw to the locking ring.

Referring to FIG. 10, a fourth preferred sliding plate variable angle locking mechanism 40 has a similar construction compared to the first preferred sliding plate variable angle locking mechanism 10 and like reference numbers are utilized to identify like features of the fourth preferred sliding plate variable angle locking mechanism 40 with a number "4" prefix replacing the "1" prefix to distinguish the features of the sliding plate variable angle locking mechanism 10 of the first preferred embodiment from the sliding plate variable angle locking mechanism 40 of the fourth preferred embodiment.

In the fourth preferred embodiment, the locking ring 450 is provided proximate the bone plate surface 460a of the bone fixation plate 460 and the bone plate hole 460c is provided proximate the upper surface of the bone plate 460. In this fourth preferred embodiment, the rotational motion of the bone fixation screw 130 being inserted into the bone fixation plate 360 could be used to impart rotation of the locking ring 450 via inwardly extending tabs 481 that provide a means for transferring the torque from the screw 130 to the locking ring 450, thereby screwing the locking ring 450 into the plate cavity 480 and imparting an upward force onto the components of the sliding plate variable angle locking mechanism 40. The locking ring 450 is driven by interaction with the bone screw 130 such that the external threads 450a of the locking ring 450 screw upwardly into the cavity threads 464a in the bone plate 460 such that the locking ring 450 moves toward the plate hole 460c.

Figure 11:
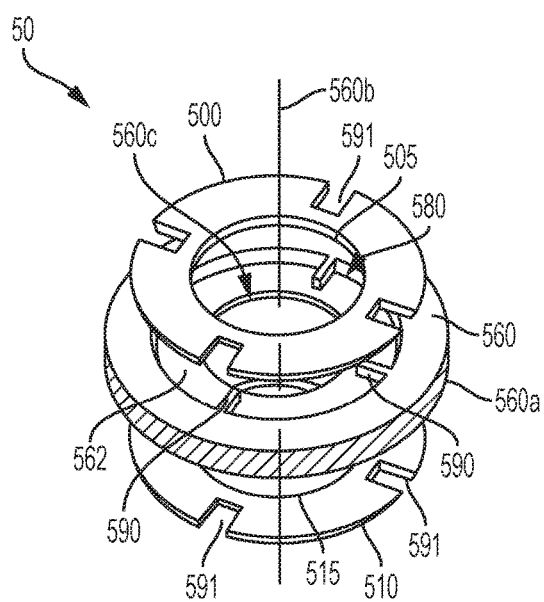
FIG. 11 is an exploded, partial cross-sectional, top perspective view of a fifth preferred embodiment of a sliding plate variable angle locking mechanism, showing upper and lower sliding plates and a bone fixation plate with a central flange.

Referring to FIG. 11, a fifth preferred sliding plate variable angle locking mechanism 50 has a similar construction compared to the first preferred sliding plate variable angle locking mechanism 10 and like reference numbers are utilized to identify like features of the fifth preferred sliding plate variable angle locking mechanism 50 with a number "5" prefix replacing the "1" prefix to distinguish the features of the sliding plate variable angle locking mechanism 10 of the first preferred embodiment from the sliding plate variable angle locking mechanism 50 of the fifth preferred embodiment.

In the fifth preferred embodiment, the shelf 562 is positioned centrally along the depth of the plate cavity 580. The shelf 562 creates a countersink below both the top and bottom surfaces of the bone fixation plate 560. In this configuration, the upper or first sliding plate 500 is capable of translating along any direction within the plane of the upper surface of the shelf 562. Likewise, the lower or second sliding plate 510 is capable of translating along any direction within the plane of the lower surface of the shelf 562. In similar fashion to the sliding plates 100, 110 of the first preferred embodiment and the corresponding description above, the sliding plates 500, 510 can be positioned such that the alignment of their central holes 505, 515 provide for a variability of orientation of the bone fixation screw 130, which describe a conical area beneath the surface of the bone fixation plate 560. Unlike the linearly restricted sliding plate motion of the first preferred embodiment above, the sliding plates 500, 510 are free to translate in any direction relative to the bone fixation plate 560 and to each other. This translational freedom, therefore, can provide for all the variability of orientation of the bone fixation screw 130 without any rotational movement of the sliding plates 500, 510 about their central axes.

In similar fashion to the first preferred embodiment above, frictional forces between the surfaces of the first sliding plate 500 and the upper surface of the shelf 562 and between the surfaces of the second sliding plate 510 and the lower surface of the shelf 562, combine to provide a means for locking the sliding plates 500, 510 in a fixed position relative to the shelf 562 and the bone plate 560. The friction between the surfaces is generated by a normal force vector acting downward on the first sliding plate 500 in the direction of the shelf 562, and an equal and opposite force vector acting upward on the second sliding plate 510 in the direction of the shelf 562. The external head threads 131 on the head 130a of the bone fixation screw 130 engage and tap into the hole circumference of the second sliding plate 510 once the screw 130 has been inserted to sufficient depth into the plate cavity 530. One or more bone fixation plate tab features 590 interact with one or more sliding plate slot features 591 to prevent rotation of the sliding plates 500, 510 during bone fixation screw insertion. The tab 590 and slot 591 features described are designed such that linear motion within the plane of the plates 500, 510 is not obstructed. As the trailing portion of the head 130a of the bone fixation screw 130 comes into contact with the upper surface of first sliding plate 500, the width of the trailing portion of the head 130a of the screw 130 prevents it from translating further into the central hole of the first sliding plate 500. Further rotation of the screw 130 continues to advance the threads 131 through the second sliding plate 510, thereby drawing the second sliding plate 510 up toward the shelf 562 in reaction to the trailing portion of the head 130a, thereby compressing against the upper surface of second sliding plate 510. The force from the advancing screw 130 from the thread interaction with the second sliding plate 510 provides the normal force vector acting upward on the second sliding plate 510 and the inability of the head 130a to translate further into the second sliding plate 510 provides the normal force vector acting downward on first sliding plate 500. As described elsewhere, the normal forces acting on each sliding plate 500, 510 creates a frictional force against the shelf 562, thereby creating sufficient frictional force in the sliding plate variable angle locking mechanism 50 to rigidly secure the bone fixation screw 130 to the plate 560.

Figure 12:
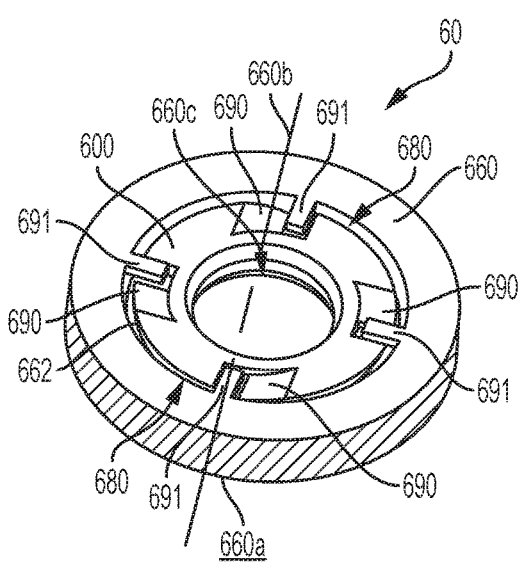
FIG. 12 is an exploded, partial cross-sectional, top perspective view of a sixth preferred embodiment of a sliding plate variable angle locking mechanism, showing upper and lower sliding plates and a bone fixation plate with a central flange, wherein the upper and lower sliding plates include wedge shaped features that, along with paired tabs extending from the bone fixation plate hole upper circumference, provide a compression means.

Referring to FIG. 12, a sixth preferred sliding plate variable angle locking mechanism 60 has a similar construction compared to the first preferred sliding plate variable angle locking mechanism 10 and like reference numbers are utilized to identify like features of the sixth preferred sliding plate variable angle locking mechanism 60 with a number "6" prefix replacing the "1" prefix to distinguish the features of the sliding plate variable angle locking mechanism 10 of the first preferred embodiment from the sliding plate variable angle locking mechanism 60 of the sixth preferred embodiment.

Referring to FIG. 12, the first sliding plate 600 of the sixth preferred embodiment includes one or more ramp features 690 extending radially into the first sliding plate 600 and located about the perimeter of the first sliding plate 600. The bone fixation plate 660 includes corresponding cantilever tabs 691 extending radially inwardly into the cavity 680 from the perimeter of the cavity 680. The threads 131 on the head 130a of the bone fixation screw 130 engage and tap into the hole 605 of the first sliding plate 600 once the screw 130 has been inserted to sufficient depth into the cavity 680. The frictional force associated with the engagement of the head threads 131 with the hole 605 in the first sliding plate 600 imparts a tangential force vector on the first sliding plate 600. The tangential force causes the first sliding plate 600 to rotate, thereby causing the ramp features 690 to engage with the tabs 691. Continued insertion of the bone fixation screw 130 further forces the ramp features 690 under the cantilevered tabs 691, thereby imparting a downward force onto the first sliding plate 600. In equivalent fashion, as the threads 131 of the head 130a of the bone fixation screw 130 engage with the first sliding plate 600, rotational forces cause the ramps features 690 to engage and slide beneath the tabs 691. Continued insertion of the bone fixation screw 130 further forces the ramp features 690 under the cantilevered tabs 691, thereby imparting a downward force onto the first sliding plate 600. The downward force on the first sliding plate 600 induces a frictional force between it and the upper surface of the shelf 662 in the cavity 680 and, likewise, the upward force on the first sliding plate 600 induces a frictional force between it and the lower surface of the cantilevered tabs 691. In combination, these frictional forces create sufficient frictional force in the sliding plate variable angle locking mechanism 60 to rigidly secure a bone fixation screw 130 relative to the plate 690.

Figure 13:
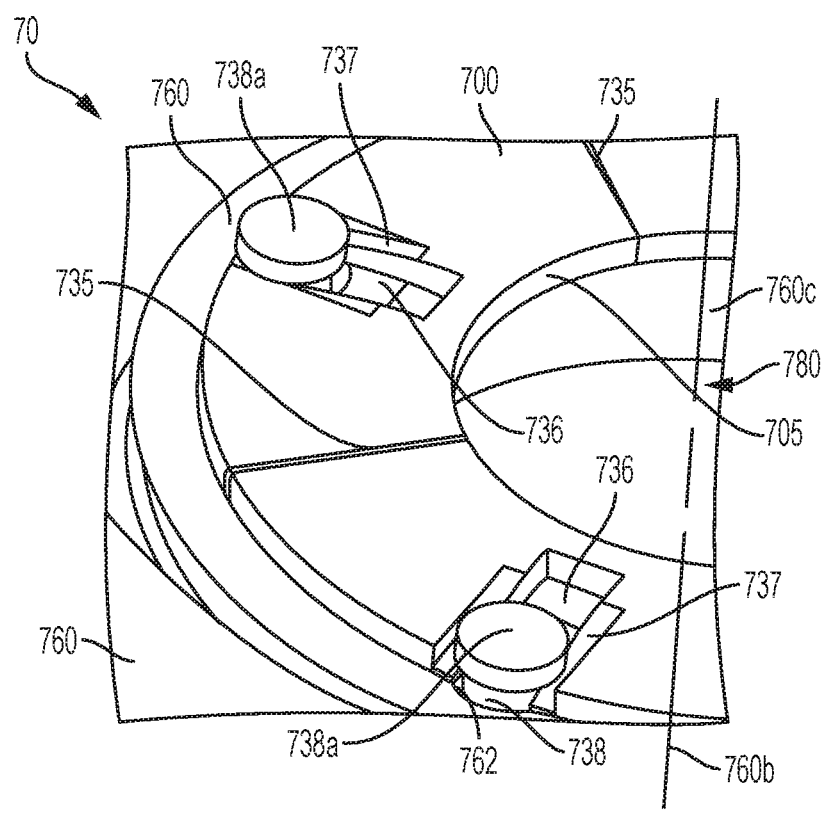
FIG. 13 is magnified, top perspective view of a seventh preferred embodiment of a sliding plate variable angle locking mechanism, showing upper and lower sliding plates and a bone fixation plate with a central flange, wherein the upper and lower sliding plates include wedge shaped features that, along with paired pins extending through the bone fixation plate flange, provide a compression means.

Referring to FIG. 13, a seventh preferred sliding plate variable angle locking mechanism 70 has a similar construction compared to the first preferred sliding plate variable angle locking mechanism 10 and like reference numbers are utilized to identify like features of the seventh preferred sliding plate variable angle locking mechanism 70 with a number "7" prefix replacing the "1" prefix to distinguish the features of the sliding plate variable angle locking mechanism 10 of the first preferred embodiment from the sliding plate variable angle locking mechanism 70 of the seventh preferred embodiment.

The seventh preferred sliding plate variable angle locking mechanism 70 is configuration to include a second sliding plate (not shown) opposite the plate hole 760c. The first sliding plate 700 is provided in a plurality of sections that are separated radially from the center of the first sliding plate 700, thereby forming joints 735. One or more slots 736 extend radially inward from the outer circumference of the first sliding plate 700. The slots 736 may be incorporated into the first sliding plate 700 between the joints 735 or may extend through the slots 736. Ramps 737 extend radially along the borders of the slots 736 such that the ramps 737 incline away from the upper surface of the sliding plate 700 with increasing distance from the center of the first sliding plate 700. Pins 738 of appropriate diameter protrude through the bone fixation plate flange through the slots 736. In configurations where the second sliding plate is located on the opposite side of the plate hole 760c, the pins 738 may protrude through the second sliding plate as well. The pins 738 include heads 738a at both ends of the pins 738, having larger diameters than the pin shaft and a width of the slots 736. The pin shafts of the pins 738 preferably have a diameter such as to allow the head 738a to interact with the ramps 737. The pins 738 are constrained on the opposite side of the plate hole 760c, either by the second sliding plate or the shelf, such that the pins 738 are restricted from translating along its long axis. The pins 738 preferably have a length such that the lower surface of the head 738a is proximate to the upper surface of the ramps 737 at points near the perimeter of the first sliding plate 700. The bone fixation screw 130, which includes the threads 131 of the head 130a, has an appropriate diameter for insertion into the hole 705 of the first sliding plate 700 to a point at which the head 130a and its threads 131 engages with the inner surface of the hole 705. Further insertion and tapping of the threads 131 into the hole 705 of the first sliding plate 700 imparts an outward radial force on the sections of the first sliding plate 700. The sections of the first sliding plate 700 translate radially outward in response to the outward force from the screw head 130a, further engaging the pin heads 738a with the ramps 737 such that the translation of the ramps 737 causes the pin head 738a to be positioned higher on the incline. The tension created in the pins 738 imparts a downward force onto the first sliding plate 700, thereby inducing frictional force between the first sliding plate 700 and the upper surface of the shelf 762. In similar fashion, the second sliding plate with the same or similar features may be incorporated into the construct on the opposite side of the bone plate 760 and, likewise, an upward force on the second sliding plate induces a frictional force between it and the lower surface of the shelf 762. In combination, these frictional forces create sufficient frictional force in the sliding plate variable angle locking mechanism to rigidly secure a bone fixation screw.

In any of the first through seventh preferred embodiments described above, the bone fixation screw 130 with the threads 131 on the head 130a designed to tap into and engage both the sliding plates, the rotating plates and the locking rings imparts additional locking forces between the bone fixation screw 130 and the bone fixation plates 160, 260, 360, 460, 560, 660, 760. An example of the internal threads 171 formed on the sliding plates 100, 110 and the rotating plate 120 of the first preferred embodiment is shown in FIG. 3c. The bone fixation screw 130, when inserted into the sliding plates 100, 110 and rotating plate 120 will both offset the plate centers 105a, 115a, 125a and create the tapped thread grooves of the internal threads 170 through and across the inner faces of the plates 100, 110, 120. Considering the threads 131 of the screw head 130a are secure from any motion except for that along the line of the groove of the internal threads 170, any motion of the screw 130 other than rotation will meet with resistive counter forces against the threads 131 of the screw head 130a. Also, considering that the threads 131 of the screw head 130a cross the interface between the plates 100, 110, 120, the restrictive engagement between the threads 131 and the internal threads 170 secures the plates 100, 110, 120 relative to each other from translation along the interface between the plates 100, 110, 120. The resulting positional rigidity between plates 100, 110, 120 due to the engagement between the screw threads 131 and the internal threads 170 adds to the frictional forces created by the configurations of the above embodiments to further enhance the capability of the sliding plate variable angle locking mechanisms 10, 20, 30, 40, 50, 60, 70 to rigidly secure the bone fixation screw 130 to the plates 160, 260, 360, 460, 560, 660, 760. This improves or enhances the strength of the engagement between the screw 130 and the plates 160, 260, 360, 460, 560, 660, 760 when the surgeon selects the variable offset angle Δ desired for the particular and desired surgical construct.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present disclosure and the appended claims.

We claim:

1. A sliding plate variable angle locking mechanism for orthopedic bone fixation, the locking mechanism comprising:
    a bone plate including a plate cavity, a bone plate surface, a plate hole adjacent the bone plate surface and a shelf formed in the plate cavity proximate the plate hole, the plate hole defining a plate hole diameter and a center axis;
    a first sliding plate having an upper surface, a lower surface and a central hole, the central hole defining a sliding plate hole diameter, the sliding plate hole diameter being smaller than the plate hole diameter, the lower surface of the first sliding plate positioned in the plate cavity in an assembled configuration, the first sliding plate constructed of a rigid bio-compatible material and configured for slidable movement within the plate cavity generally perpendicular relative to the center axis;
    a locking ring movably mountable to the bone plate, the locking ring having a locking ring hole, the locking ring hole defining a locking ring hole diameter, the locking ring hole diameter being greater than the sliding plate hole diameter; and
    a bone screw having a head with head threads and a shaft, the head threads defining a bone screw head diameter, the bone screw head diameter being greater than the sliding plate hole diameter, the head threads configured to form internal threads in the central hole of the first sliding plate when the bone screw is driven into the first sliding plate in the plate cavity.

2. The locking mechanism of claim 1, further comprising:
    a second sliding plate having an upper surface, a lower surface and a central hole, the second sliding plate positioned within the cavity and configured for slidable movement within the cavity in an assembled configuration.

3. The locking mechanism of claim 2, further comprising:
    additional sliding plates, wherein the additional sliding plates and the second sliding plate are positioned between the first sliding plate and the locking ring in the assembled configuration.

4. The locking mechanism of claim 1, further comprising:
    a rotating plate having a central hole and downwardly depending sliding guides, the sliding guides cooperating with linear side guides on the first sliding plate to generally limit rotational movement of the first sliding plate relative to the rotating plate in the assembled configuration.

5. The locking mechanism of claim 1, wherein the locking ring includes external threads and the plate cavity includes cavity threads, the external threads engageable with the cavity threads to releasably mount the locking ring to the bone plate.

6. The locking mechanism of claim 1, further comprising:
    a second sliding plate having a central hole; and
    a rotating plate having a central hole, the central hole of the second sliding plate and the central hole of the rotating plate having a diameter that is the same as the sliding plate hole diameter.

7. The locking mechanism of claim 1, wherein the first sliding plate is constructed of a first material and the bone screw is constructed of a second material, the second material having a greater hardness than the first material.

8. The locking mechanism of claim 1, wherein the locking ring includes circular features, the circular features configured for engagement with a tool to apply torque to the locking ring.

9. The locking mechanism of claim 1, wherein the bone screw, the first sliding plate and the plate cavity are configured to permit engagement between the bone screw and the bone plate in a locked configuration wherein the head threads are engaged with the internal threads in the central hole of the first sliding plate such that the bone screw defines an offset angle relative to a center axis of the bone plate.

10. The locking mechanism of claim 9, wherein the bone screw, first sliding plate and bone plate are configured such that the shaft of the bone screw may be locked at a plurality of the offset angles relative to the bone plate within a conical area beneath the bone plate.

11. The locking mechanism of claim 9, wherein the offset angle is within a range of zero degrees to twenty-five degrees.

12. A sliding plate variable angle locking mechanism for orthopedic bone fixation, the locking mechanism comprising:
    a bone plate including a bone plate surface, a plate hole adjacent the bone plate surface and a shelf, the plate hole defining a plate hole diameter;
    a first sliding plate having an upper surface, a lower surface and a central hole, the central hole defining a sliding plate hole diameter, the sliding plate hole diameter being smaller than the plate hole diameter, the first sliding plate configured for slidable movement relative to the bone plate;
    a second sliding plate having an upper surface, a lower surface and a central hole, the second sliding plate configured for slidable movement relative to the bone plate and the first sliding plate in an assembled and unlocked configuration with the second sliding plate positioned between the shelf and the first sliding plate;
    a rotating plate having a central hole, a lower surface and an upper surface, the lower surface of the rotating plate positioned on the upper surface of the first sliding plate in the assembled configuration;
    a locking ring movably mountable to the bone plate, the locking ring having a locking ring hole, the locking ring hole defining a locking ring hole diameter, the locking ring hole diameter being greater than the sliding plate hole diameter; and
    a bone screw having a head with head threads and a shaft, the head threads defining a bone screw head diameter, the bone screw head diameter being greater than the sliding plate hole diameter, the head threads configured to form internal threads in the central hole of the first sliding plate and the second sliding plate when the bone screw is driven into the first sliding plate and the second sliding plate in the assembled and locked configuration.

13. The locking mechanism of claim 12, wherein the bone plate includes a plate cavity, the first sliding plate, the second sliding plate and the rotating plate substantially positioned within the plate cavity in the assembled configuration.

14. The locking mechanism of claim 13, wherein the plate cavity includes cavity threads proximate an upper surface of the bone plate and the locking ring includes external threads that are engageable with the cavity threads.

15. The locking mechanism of claim 14, wherein friction forces are increased at interfaces between the second sliding plate and the shelf, the second sliding plate and the first sliding plate, the first sliding plate and the rotating plate and the rotating plate and the locking ring as the locking ring is screwed into the plate cavity.

16. The locking mechanism of claim 12, wherein the first sliding plate includes a center within its central hole, the second sliding plate includes a center within its central hole and the rotating plate includes a center within its central hole, the first sliding plate, the second sliding plate and the rotating plate slidable relative to each other to align the centers of the first sliding plate, the second sliding plate and the rotating plate along a sliding plate longitudinal axis, the position of the sliding plate longitudinal axis relative to a center axis of the plate hole defining an offset angle.

17. The locking mechanism of claim 16, wherein the rotating plate includes a pair of sliding guides on opposing sides that define openings between the pair of sliding guides.

18. The locking mechanism of claim 17, wherein the first and second sliding plates extend through the openings in the assembled configuration.

19. The locking mechanism of claim 12, wherein the shelf is formed in a plate cavity adjacent the plate hole.

20. The locking mechanism of claim 12, wherein the head threads are constructed of a first material and the first sliding plate is constructed of a second material, the first material having a hardness greater than the second material.

* * * * *